United States Patent
Cesarczyk et al.

Patent Number: 6,165,156
Date of Patent: Dec. 26, 2000

[54] DEVICE AND METHOD FOR FASTENING A CATHETER

[75] Inventors: Edward J. Cesarczyk, North Easton; Richard B. Freeman, Wellesley, both of Mass.

[73] Assignee: Avitar, Inc., Canton, Mass.

[21] Appl. No.: 08/947,235

[22] Filed: Oct. 8, 1997

Related U.S. Application Data

[63] Continuation of application No. 08/630,875, Apr. 2, 1996, abandoned.

[51] Int. Cl.[7] .................................................. A61M 5/32
[52] U.S. Cl. ................. 604/180; 604/174; 128/DIG. 26; 602/41; 602/54; 602/57
[58] Field of Search .................... 604/174, 178, 604/179, 180; 128/DIG. 26; 602/41–43, 54–60, 52

[56] References Cited

U.S. PATENT DOCUMENTS

| | | | |
|---|---|---|---|
| 3,046,984 | 7/1962 | Eby | 604/180 |
| 3,918,446 | 11/1975 | Buttaravoli | 128/DIG. 26 |
| 3,973,565 | 8/1976 | Steer | 604/180 |
| 4,324,236 | 4/1982 | Gordon | 604/180 |
| 4,490,141 | 12/1984 | Lacko | 604/180 |
| 4,645,492 | 2/1987 | Weeks | 604/174 |
| 4,705,040 | 11/1987 | Mueller et al. | 128/334 |
| 4,941,882 | 7/1990 | Ward et al. | 604/180 |
| 5,073,166 | 12/1991 | Parks et al. | 609/93 |
| 5,100,396 | 3/1992 | Zamierowski | 604/305 |
| 5,279,574 | 1/1994 | Forren | 604/174 |
| 5,338,308 | 8/1994 | Wilk | 604/180 |
| 5,364,367 | 11/1994 | Banks et al. | 604/174 |
| 5,372,589 | 12/1994 | Davis | 604/174 |
| 5,384,174 | 1/1995 | Ward et al. | 428/40 |
| 5,755,681 | 5/1998 | Plews | 602/58 |
| 5,885,254 | 3/1999 | Matyas | 604/180 |
| 5,891,074 | 4/1999 | Cesarczyk | 602/42 |
| 5,902,275 | 5/1999 | Dobkin | 604/174 |
| 5,947,917 | 9/1999 | Carte et al. | 602/52 |
| 5,947,931 | 10/1999 | Bierman | 604/180 |
| 5,951,521 | 9/1999 | Mastrototaro et al. | 604/174 |
| 5,968,000 | 10/1999 | Harrison et al. | 602/41 |
| 5,973,221 | 10/1999 | Collyer et al. | 602/46 |

FOREIGN PATENT DOCUMENTS

| | | |
|---|---|---|
| 0 082 596 A1 | 6/1983 | European Pat. Off. . |
| 0 638 301 A1 | 2/1995 | European Pat. Off. . |
| 2 202 749 | 10/1988 | United Kingdom . |
| 2202749 | 10/1988 | United Kingdom . |
| WO 92/19290 | 11/1992 | WIPO . |

*Primary Examiner*—Corrine McDermott
*Assistant Examiner*—Cris L Rodriguez
*Attorney, Agent, or Firm*—George W. Neuner; Dike, Bronstein, Roberts And Cushman LLP

[57] ABSTRACT

A fastening device has a support layer, an adhesive layer on one side of the support layer, and a removable liner on the adhesive layer opposite to the support layer, the support layer having an opening therethrough. The device facilitates securing of a catheter or like assembly to a patient. A preferred catheter assembly includes the fastening device, a needle, a cannula and a hub attached to the cannula.

17 Claims, 5 Drawing Sheets

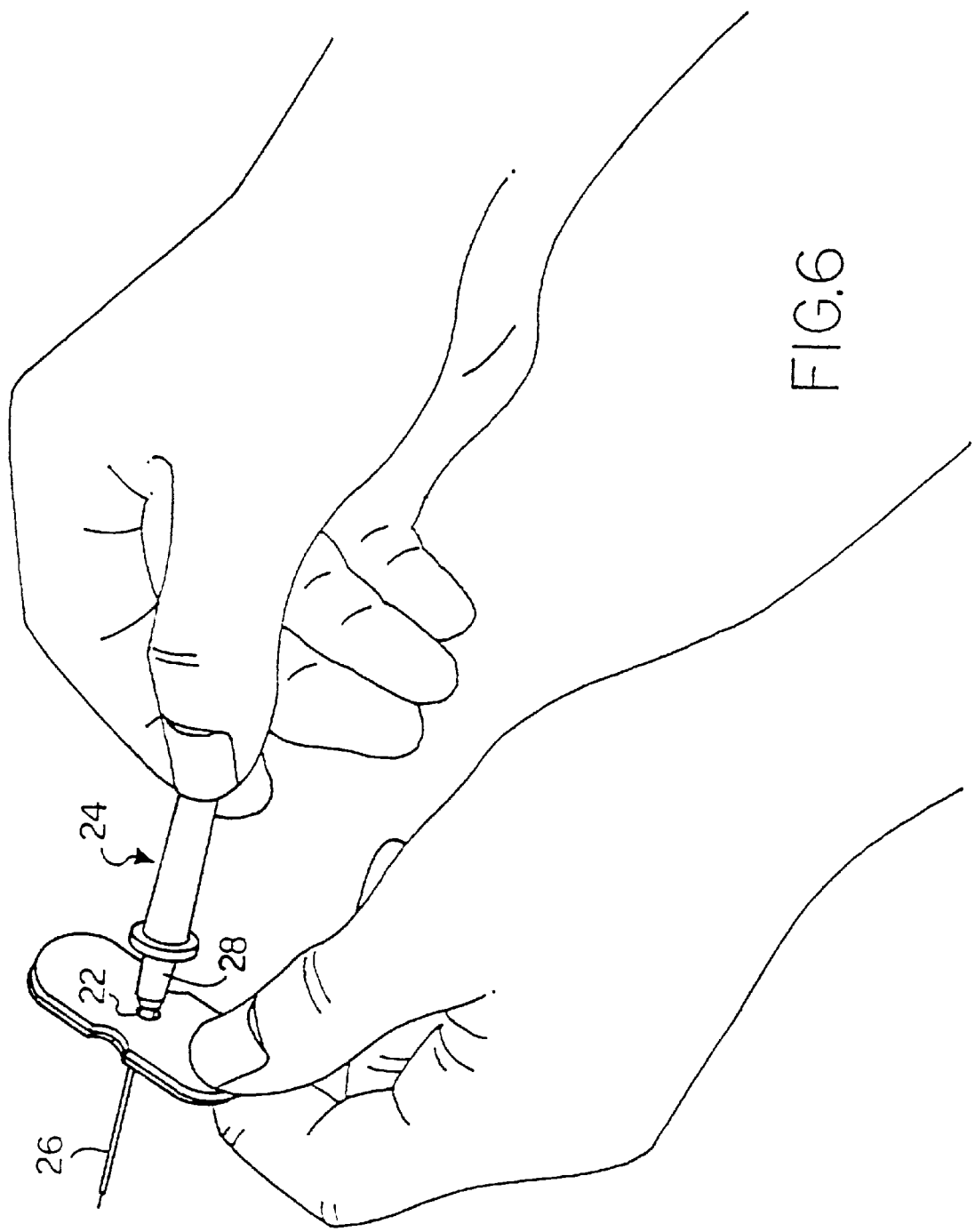

DEVICE AND METHOD FOR FASTENING A CATHETER

This application is a continuation of application Ser. No. 08/630,875 filed on Apr. 02, 1996 now abandoned.

INTRODUCTION

The present invention relates to a fastening device and method for fastening a catheter or like device to a patient, particularly to a fastening device that is adhesively attached to the patient and, more particularly, to a catheter unit including the fastening device.

BACKGROUND OF THE INVENTION

Presently, for example, intravenous catheters are attached to the skin with any one of a variety of standard hospital grade tapes or like fasteners. This procedure typically is initiated by taking an intravenous catheter with its corresponding needle and inserting it through the skin into an appropriate position within a vein usually located on the back of the hand or on the arm. After checking for appropriate flow, the needle is then partially retracted such that the cannula portion remains in the vein with the needle portion not yet completely removed. Hospital grade tape, which has been cut to predetermined lengths, is fastened around the catheter hub and then to the patient. This procedure usually requires two hands to manipulate and adjust the tape into the proper position while simultaneously holding the catheter and needle in its position. The needle is then removed and the intravenous line is connected to the hub of the inserted catheter. This known technique varies somewhat in its configuration because it is applied on an individual basis.

The methodology of holding a catheter and needle which has been previously inserted into a blood vessel while taping said catheter with several pieces of tape can be time consuming and somewhat cumbersome for the clinician administering the procedure as well as discomforting for the patient due to inadvertent manipulation of the catheter. Additionally, the extent to which hospital grade tape secures a catheter to a patient can, at times, be inadequate.

A common problem with intravenous catheters is that they can become loose or fall out completely, requiring additional insertions. It is important to maintain intravenous access at the same point for as long as possible to reduce the likelihood of infection, especially with regard to patients that will need an intravenous connection for an extended period of time or elderly patients due to their decreased resistance to infection.

Phlebitis or inflammation of a vein is another major concern with respect to an intravenous site. Manipulation or agitation of the catheter due to inadequate fastening can increase the likelihood of phlebitis also requiring the need to locate a new access point.

It is therefore desirable to provide a device that fastens a catheter to a patient securely, lessens the likelihood of inadvertent manipulation and is consistent with regard to its application. Further, it is desirable to provide a method that is convenient to administer, expedient and minimizes patient discomfort.

BRIEF SUMMARY OF INVENTION

The fastening device of the present invention comprises a support layer of a pliant material, a layer of adhesive on one side of the support layer and an adhesive liner removably attached to the adhesive layer. The fastening device is configured to fit over the hub of an intravenous catheter or like device.

The catheter assembly typically comprises a cannula, hub and a removable needle used to assist with the insertion of the cannula. The adhesive liner of the fastening device is conveniently provided in two portions, e.g., creating two halves of the liner, thereby allowing the center portion of the support to stretch. An opening is located in the center of the fastening device to permit the needle and cannula to be guided through the fastening device so that the fastening device can be positioned on the hub of the catheter.

It is preferred that the diameter of the opening in the fastening device is less than the outside diameter of the catheter hub. Thus, that portion of the support stretches when the hub is inserted into the opening. Tension is thus created around the center of the fastening device. The tension not only holds the fastening device onto the hub prior to insertion but also positions the fastening device in a configuration such that its end portions are suspended away from the end portion of the needle and cannula. Due to that configuration of the fastening device on the hub, the adhesive liner portions begin to peel away from the adhesive layer outwardly from the center of the support layer, facilitating removal of the liner for adhesion of the fastening device to the patient.

The method of attachment of the present invention differs from that which is currently used in that the fastening device of the invention is attached to the hub of the catheter prior to insertion. This can be accomplished by the clinician, or the fastening device can be provided on the hub as a component of an assembled complete intravenous catheter set.

When the fastening device is not assembled with the catheter as a set, to use the fastening device, the device is removed from its sterile package and is placed on the hub of a catheter by threading the catheter needle and cannula through the center opening of the fastening device so that the adhesive side of the fastening device is facing the end portion of the needle. The opening is stretched over the hub, thereby causing the fastening device to retract into its proper position with the ends of the device extending away from the catheter needle and allowing the adhesive liner portions to begin to peel away from the adhesive. An intravenous catheter with its corresponding needle, for example, is then inserted through the skin into a suitable position within a vein usually located on the back of the hand or arm. After checking for appropriate insertion into the blood vessel, the needle is then partially retracted such that the cannula portion remains in the vein with the needle portion not yet completely removed. While holding the needle and catheter steady by the needle handle with one hand, the liner portions of the fastening device can be conveniently removed with the other hand and the fastening device end portions adhered securely to the skin on either side of the hub. Because the support is conveniently folded away from the needle due to the fit of the fastening device around the hub, the adhesive readily contacts the patient's skin as well as the hub of the catheter, securely anchoring the hub to the skin. Additionally, when the fastening device is in the anchored position, a portion of the support is located between the patients skin and the hub, promoting proper cannula angle as well as preferably providing additional patient comfort due to the resilience of the support material. The needle is then removed and the intravenous line is connected to the hub of the inserted catheter in the usual manner.

Secure anchoring of the catheter is achieved with the fastening device of the present invention by inserting the catheter hub through the undersized opening located in the center of the fastening device and wrapping the adhesive side of the support around the top of the hub. Anchoring the catheter in this manner with the fastening device of the present invention reduces the likelihood of cannula manipulation within the vein or of the catheter loosening, thereby reducing the potential of phlebitis and assisting in permitting access at the site for longer periods. Attaching the fastening device to the hub prior to insertion permits the clinician to conveniently secure the catheter to the patient with one hand, allowing the other hand to stabilize the position of the catheter. This fastening device and method provides for an expedient procedure which minimizes inadvertent manipulation of the catheter and needle and, therefore, minimizes patient discomfort.

BRIEF DESCRIPTION OF THE DRAWINGS

FIG. 6 illustrates a catheter being inserted through a fastening device in accord with an embodiment of the present invention.

DETAILED DESCRIPTION OF THE INVENTION INCLUDING PREFERRED EMBODIMENTS

Figure 3:
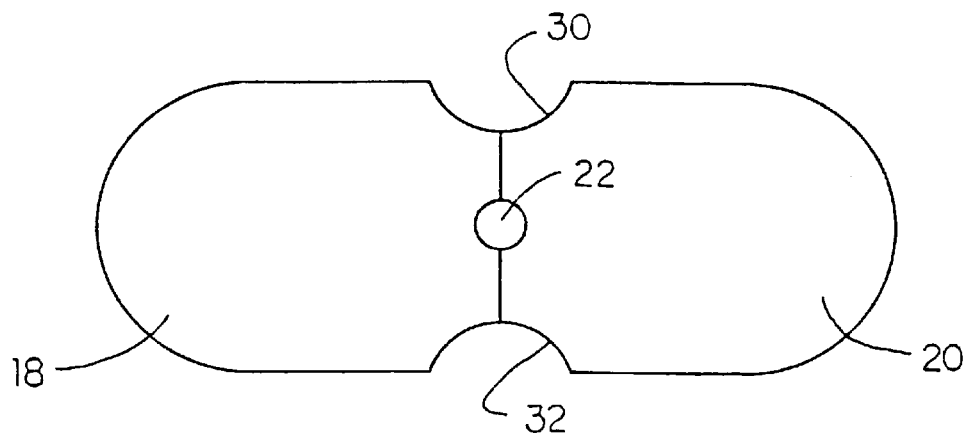
FIG. 3 is a bottom view of the device of FIG. 1.
Figure 4:
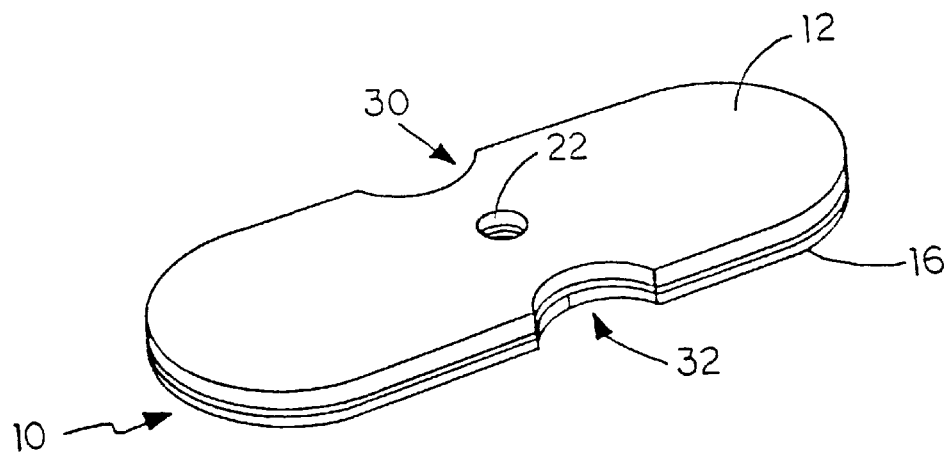
FIG. 4 is an isometric view of the device of FIG. 1.
Figure 5:
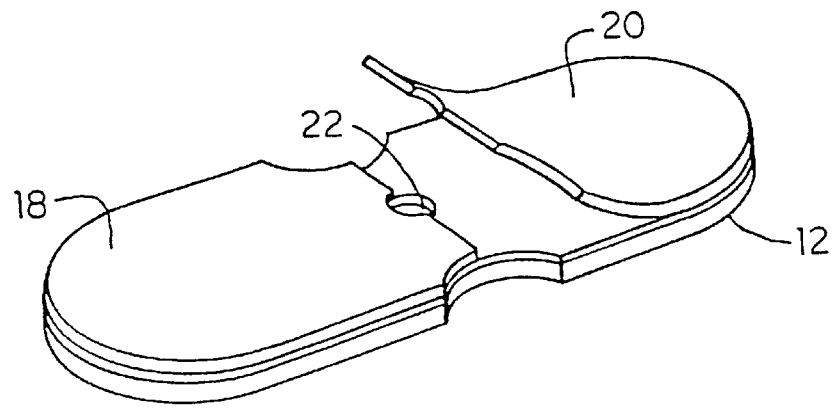
FIG. 5 is another isometric view of the device of FIG. 1 illustrating the release characteristic of liner 20.

With reference to the drawings (FIGS. 1–5), one embodiment of a fastening device 10 comprises a flexible support layer 12 with an opening 22, an adhesive layer 14 and a liner 16. The adhesive layer 14 is applied to the support layer and the liner 16 is preferably attached to the adhesive layer in two pieces 18,20 (see FIG. 3).

The support layer preferably comprises a pliant material, more preferably a resilient material such as a foamed polymeric material, having a preferred thickness of about 0.002 inch to about 0.250 inch, more preferably about 0.030 inch to about 0.065 inch. Conveniently, the support layer is approximately 0.031 inch (1/32 inch) thick in the embodiment illustrated in FIGS. 1–5. As is readily apparent to the skilled artisan, the thickness can vary depending upon particular applications. Support layer materials can be selected from, for example, open or closed cell polyethylene foam, open or closed cell polyurethane foam, polyvinylchloride foam, polyethylene film, ethylvinylacetate film, polyethylene/ethylvinylacetate film, spun-laced polyester or rubber. Examples of materials preferred for the support layer are ARcare 7144 closed cell polyethylene foam produced by Adhesive Research, Inc. and 1773 closed cell polyethylene foam produced by 3M.

Typically, the opening in the fastening device has a diameter of about 0.062 inch or more, preferably in the range of from about 0.125 to about 0.156 inch, to accommodate standard size catheters. Preferably, the opening is sized to accommodate a range of catheter sizes. The diameter of the opening will depend upon the particular strength and pliant characteristics of the material used for the support layer.

The adhesive layer can be a liquid, paste or double sided tape applied to the support. It is preferred that the adhesive be of a non-sensitizing type adhesive such as, for example, hypoallergenic, pressure sensitive, acrylate adhesive. Preferably the adhesive has a peel strength (adhesion to steel) of about 10 oz/in. to about 60 oz/in., more preferably about 35 oz/in. to about 45 oz/in. Preferably, the adhesive has a minimum 180 degree peel strength of about 40 oz/in. It is further advantageous that the adhesive have, moisture absorbing, anti-bacterial and/or anti-fungal properties to help reduce the possibility of infection at the site of insertion.

The liner can be made of a plastic or plastic-like substance such as, for example, a siliconized polycoated Kraft release paper or Teflon-coated paper. The liner should be easily removable from the adhesive, being pealed therefrom with little force on the part of the clinician, thereby minimizing the possibility of jarring or moving the catheter when fastening to a patient.

Manufacturing of the fastening device can be accomplished by assembling the layers and utilizing a standard die-cutting technique known in the industry. Those skilled in the art will recognize other suitable materials and means of manufacturing the fastening device.

Figure 1:
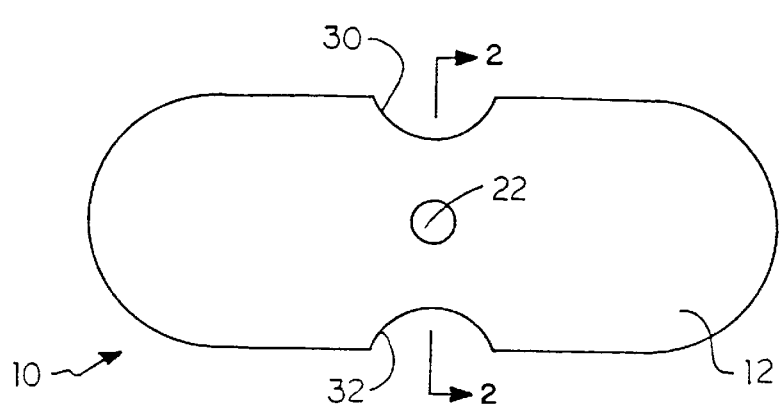
FIG. 1 is a top view of a fastening device in accord with a preferred embodiment of the present invention.
Figure 2:
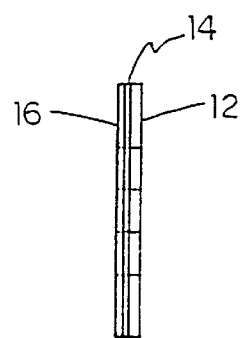
FIG. 2 is a cross sectional view of the device shown in FIG. 1.
Figure 7:
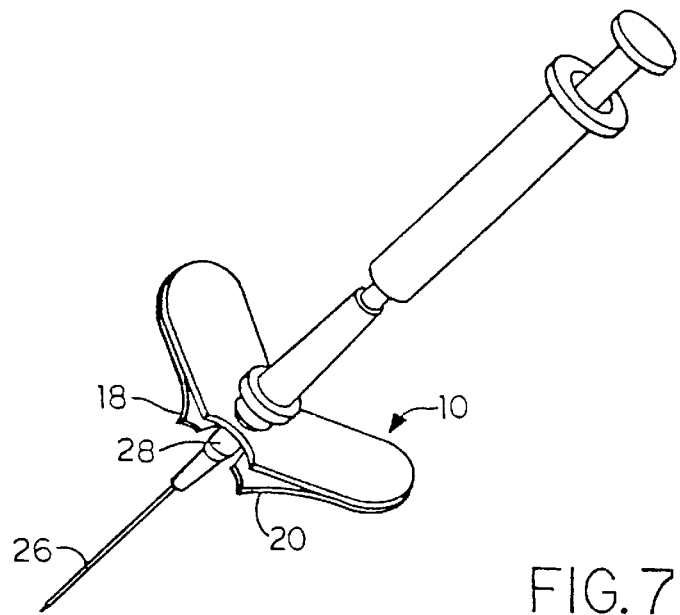
FIG. 7 illustrates another embodiment of the invention wherein a fastening device and a catheter are assembled.
Figure 8:
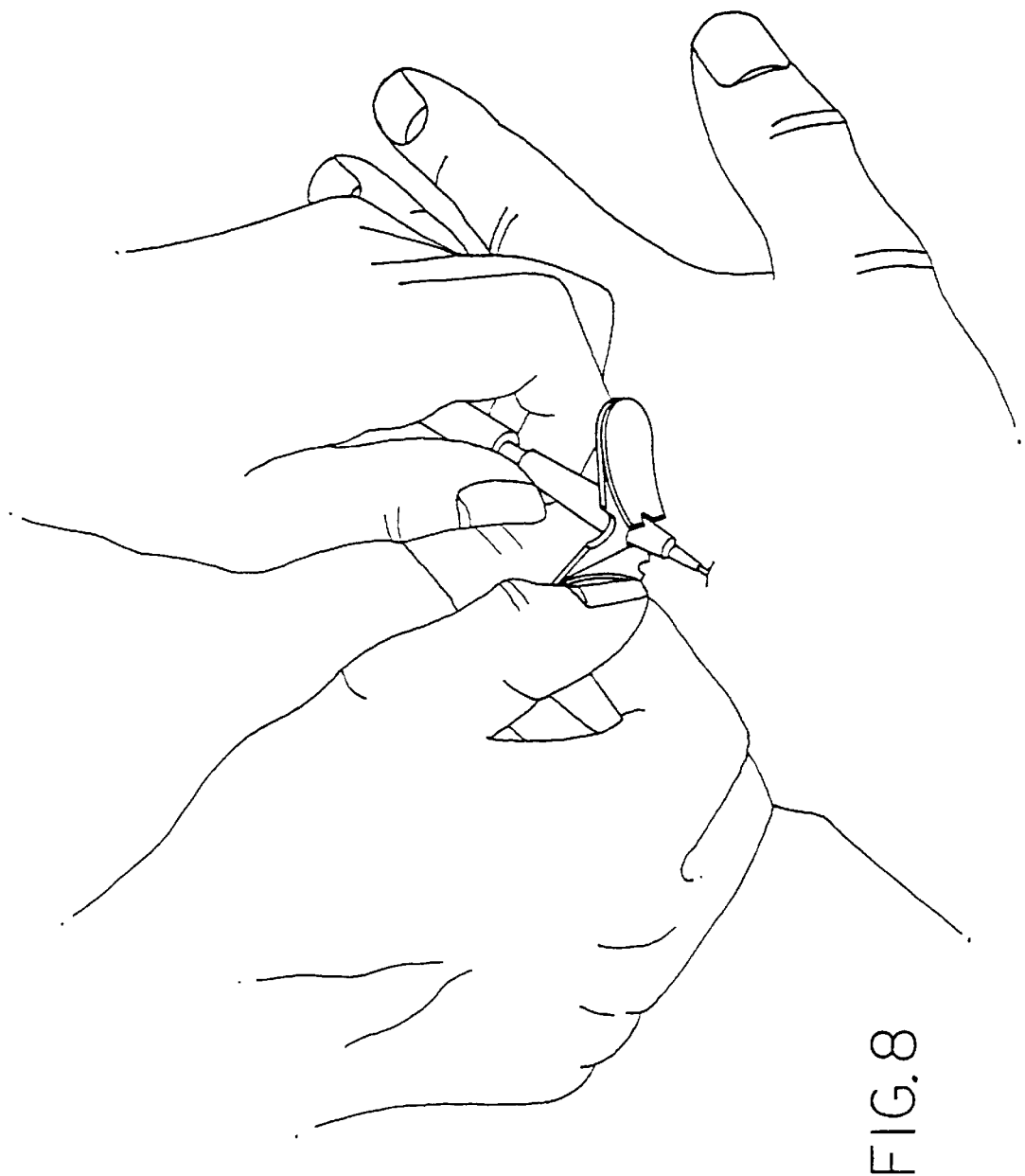
FIG. 8 illustrates the configuration of a fastening device of the invention during insertion of the catheter into a patient.
Figure 9:
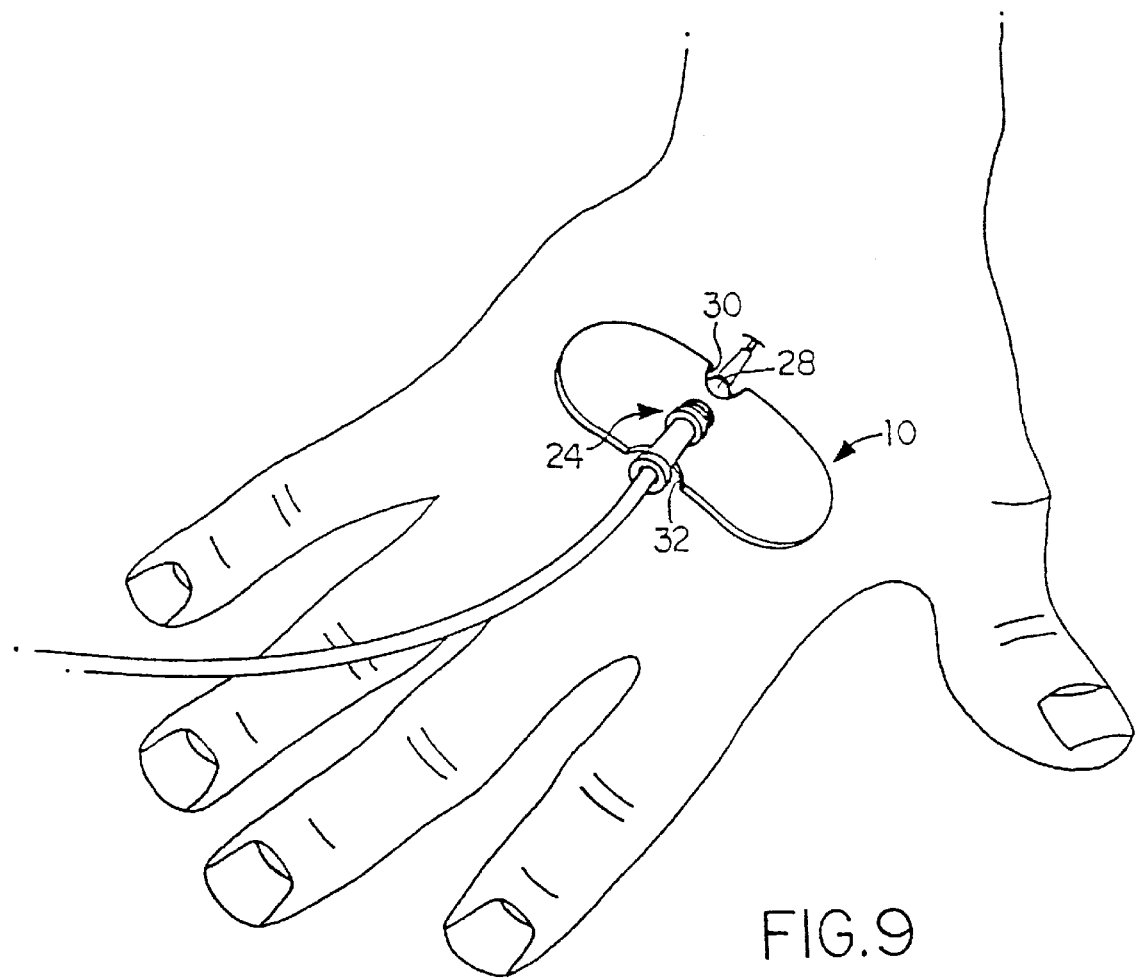
FIG. 9 illustrates a catheter with attached fastening device after insertion and affixation to a patient.

The fastening device 10 is used by inserting the hub 28 of a catheter assembly 24 into the opening 22 in the fastening device, as shown in FIG. 6. It is preferred that the opening 22 be slightly smaller than the hub 28 in order to assure tension between the fastening device and the catheter hub. Thus, the fastening device support layer stretches around the opening to fit snugly around the catheter hub 28 and the liner portions 18,20 separate to facilitate removal. When the fastening device is pulled onto the catheter hub, the liner pieces 18,20 begin to curl outward away from the hub 28 to enable their being peeled from the adhesive layer (see FIG. 7). Once the fastening device 10 is positioned on the hub 28, the needle and cannula are inserted, for example, into a patient's vein (FIG. 8). Once properly positioned in the vein, the liner pieces are removed from the fastening device 10. The fastening device is then folded down to adhere to the patient's skin and the hub 28 of the catheter assembly 24 (FIG. 9).

The clinician can hold the catheter assembly 24 in one hand and remove the liner pieces 18, 20 with the other, pressing the adhesive layer 14 and support layer 12 against both the patient's skin and the catheter hub 28, securing them together. This enables the clinician to hold the inserted catheter steadily in place with the other hand, preventing any discomfort to the patient from accidental movement of the needle and cannula.

It is preferred that the fastening device 10 contain at least one notch, axially aligned with the opening 22, to facilitate manipulation of the fastening device around the catheter hub during the fastening process. It is more preferred that the fastening device have two notches 30,32 axially aligned with the opening 22. The notches 30,32, are shaped to accommodate the shape of the catheter hub 28 when the fastening device is manipulated to attach the adhesive layer 14 to the hub 28 and to the patient's skin. The notches can be substantially 'U' or 'V' shaped, but are preferably semi-circular, as shown in the drawings.

The fastening device can be packaged in its own sterile wrapper. Alternatively, the fastening device can be assembled with a catheter unit in a sterile package.

Although the invention has been described in detail with reference to the preferred embodiments thereof, it will be appreciated by those skilled in the art, upon considering the present specification and drawings, that modifications and/or improvements may be made within the spirit and scope of the invention.

We claim:

1. A one-piece fastening device having two opposing ends and two opposing lateral edges extending between the two ends, said device comprising an one-piece support layer, an adhesive layer on one side of the support layer, and a removable liner on the adhesive layer opposite to the support layer, the support layer having an opening therethrough, wherein the opening does not communicate with the edges of the device and wherein said removable liner has an opening commensurate with the opening in the support layer and has two parts, each part having one end on the adhesive layer adjacent to an end of the fastening device and an opposite end of each part extending between the lateral edges of the fastening device, the two parts abutting in a position where a line drawn through the abutting parts would extend through the opening.

2. The fastening device of claim 1 wherein the support layer comprises of a pliant material.

3. The fastening device of claim 2 wherein the pliant material comprises a foamed polymeric material.

4. The fastening device of claim 2 wherein the pliant material comprises a closed cell polyethylene foam.

5. The fastening device of claim 1 wherein the removable liner comprises two adjacent pieces, each piece extending substantially to one side of the opening.

6. The fastening device of claim 5 wherein the adjacent pieces are a polymeric material that releases from the adhesive layer.

7. The fastening device of claim 1 wherein the adhesive layer contains an antibacterial agent.

8. The fastening device of claim 1 wherein the adhesive layer contains an antifungal agent.

9. The fastening device of claim 1 wherein the opening is centrally located.

10. The fastening device of claim 9 wherein the opening has a diameter of about 0.062 inch or greater.

11. The fastening device of claim 10 wherein the diameter is about 0.125 to about 0.156 inch.

12. The fastening device of claim 9 having at least one notch aligned axially with the opening.

13. The fastening device of claim 12 wherein the notch is semicircular.

14. The fastening device of claim 13 wherein the notch is 'U' shaped.

15. The fastening device of claim 13 wherein the notch is 'V' shaped.

16. An assembly comprising a catheter and the fastening device of claim 1, wherein the catheter comprises a catheter hub and the fastening device circumscribes and is frictionally adhered to the catheter hub.

17. A method of using the fastening device of claim 1 comprising:
   a) inserting a catheter comprising a cannula, needle and catheter hub through the opening of the fastening device, thereby circumscribing the catheter hub with the fastening device;
   b) pulling the fastening device onto the catheter hub to bend the fastening device away from the needle and toward the catheter hub;
   c) inserting the catheter needle and cannula into a blood vessel of a patient;
   d) removing the liner from the fastening device; and
   e) adhering the fastening device to the patient and to the catheter hub.

* * * * *